(12) United States Patent
Shireman

(10) Patent No.: US 8,535,243 B2
(45) Date of Patent: Sep. 17, 2013

(54) MEDICAL DEVICES AND TAPERED TUBULAR MEMBERS FOR USE IN MEDICAL DEVICES

(75) Inventor: Brice L. Shireman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 301 days.

(21) Appl. No.: 12/207,842

(22) Filed: Sep. 10, 2008

(65) Prior Publication Data

US 2010/0063480 A1   Mar. 11, 2010

(51) Int. Cl.
*A61B 5/00* (2006.01)

(52) U.S. Cl.
USPC .......................................................... 600/585

(58) Field of Classification Search
USPC ........................................ 600/585; 604/528
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Brian Szmal
*Assistant Examiner* — H. Q. Nguyen
(74) *Attorney, Agent, or Firm* — Seager, Tufte & Wickhem, LLC

(57) ABSTRACT

Medical devices and methods for making and using the same. An example medical device may include a metallic tubular member including a tube wall defining an inner diameter and having a wall thickness. The tubular member may have a plurality of slots formed therein. The tubular member may also include first portion having a first length. The tube wall may have a substantially constant wall thickness across the first length. The tubular member may also include a second portion having a second length. The tube wall may thin so that the inner diameter increases across the second length.

17 Claims, 18 Drawing Sheets

(56) References Cited

U.S. PATENT DOCUMENTS

| | | | |
|---|---|---|---|
| 3,890,977 | A | 6/1975 | Wilson |
| 3,906,938 | A | 9/1975 | Fleischhacker |
| 4,000,672 | A | 1/1977 | Sitterer et al. |
| 4,003,369 | A | 1/1977 | Heilman et al. |
| 4,020,829 | A | 5/1977 | Willson et al. |
| 4,142,119 | A | 2/1979 | Madey |
| 4,215,703 | A | 8/1980 | Wilson |
| 4,330,725 | A | 5/1982 | Hintz |
| 4,425,919 | A | 1/1984 | Alston, Jr. et al. |
| 4,476,754 | A | 10/1984 | Ducret |
| 4,482,828 | A | 11/1984 | Vergues et al. |
| 4,545,390 | A | 10/1985 | Leary |
| 4,563,181 | A | 1/1986 | Wijayarathna et al. |
| 4,574,670 | A | 3/1986 | Johnson |
| 4,580,551 | A | 4/1986 | Siegmund et al. |
| 4,583,404 | A | 4/1986 | Bernard et al. |
| 4,635,270 | A | 1/1987 | Gürs |
| 4,665,906 | A | 5/1987 | Jervis |
| 4,676,249 | A | 6/1987 | Arenas et al. |
| 4,721,117 | A | 1/1988 | Mar et al. |
| 4,737,153 | A | 4/1988 | Shimamura et al. |
| 4,763,647 | A | 8/1988 | Gambale |
| 4,774,949 | A | 10/1988 | Fogarty |
| 4,781,092 | A | 11/1988 | Gaiser |
| 4,781,186 | A | 11/1988 | Simpson et al. |
| 4,786,220 | A | 11/1988 | Fildes et al. |
| 4,790,331 | A | 12/1988 | Okada et al. |
| 4,800,890 | A | 1/1989 | Cramer |
| 4,811,743 | A | 3/1989 | Stevens |
| 4,827,941 | A | 5/1989 | Taylor et al. |
| 4,831,858 | A | 5/1989 | Yoshizawa |
| 4,832,047 | A | 5/1989 | Sepetka et al. |
| 4,846,186 | A | 7/1989 | Box et al. |
| 4,846,193 | A | 7/1989 | Tremulis et al. |
| 4,867,173 | A | 9/1989 | Leoni |
| 4,875,489 | A | 10/1989 | Messner et al. |
| 4,884,579 | A | 12/1989 | Engelson |
| 4,911,148 | A | 3/1990 | Sosnowski et al. |
| 4,917,102 | A | 4/1990 | Miller et al. |
| 4,922,164 | A | 5/1990 | Jacobsen et al. |
| 4,922,777 | A | 5/1990 | Kawabata |
| 4,932,959 | A | 6/1990 | Horzewski et al. |
| 4,934,380 | A | 6/1990 | Toledo |
| 4,953,553 | A | 9/1990 | Tremulis |
| 4,954,022 | A | 9/1990 | Underwood et al. |
| 4,955,384 | A | 9/1990 | Taylor et al. |
| 4,955,862 | A | 9/1990 | Sepetka |
| 4,960,410 | A | 10/1990 | Pinchuk |
| 4,964,409 | A | 10/1990 | Tremulis |
| 4,966,163 | A | 10/1990 | Kraus et al. |
| 4,968,306 | A | 11/1990 | Huss et al. |
| 4,973,321 | A | 11/1990 | Michelson |
| 4,985,022 | A | 1/1991 | Fearnot et al. |
| 4,989,608 | A | 2/1991 | Ratner |
| 4,990,143 | A | 2/1991 | Sheridan |
| 4,994,069 | A | 2/1991 | Ritchart et al. |
| 4,998,923 | A | 3/1991 | Samson et al. |
| 5,007,434 | A | 4/1991 | Doyle et al. |
| 5,009,137 | A | 4/1991 | Dannatt |
| 5,040,543 | A | 8/1991 | Badera et al. |
| 5,050,606 | A | 9/1991 | Tremulis |
| 5,052,404 | A | 10/1991 | Hodgson |
| 5,059,177 | A | 10/1991 | Alcebo et al. |
| 5,063,935 | A | 11/1991 | Gamble |
| 5,065,769 | A | 11/1991 | De Toledo |
| 5,095,915 | A | 3/1992 | Engelson |
| 5,106,455 | A | 4/1992 | Jacobsen et al. |
| 5,109,830 | A | 5/1992 | Cho |
| 5,125,395 | A | 6/1992 | Adair |
| 5,135,531 | A | 8/1992 | Shiber |
| 5,144,959 | A | 9/1992 | Gambale et al. |
| 5,147,317 | A | 9/1992 | Shank et al. |
| 5,181,668 | A | 1/1993 | Tsuji et al. |
| 5,205,830 | A | 4/1993 | Dassa et al. |
| 5,211,183 | A | 5/1993 | Wilson |
| 5,228,441 | A | 7/1993 | Lundquist |
| 5,238,004 | A | 8/1993 | Sahatjian et al. |
| 5,242,759 | A | 9/1993 | Hall |
| 5,243,996 | A | 9/1993 | Hall |
| 5,250,069 | A | 10/1993 | Nobuyoshi et al. |
| 5,254,106 | A | 10/1993 | Feaster |
| 5,254,107 | A | 10/1993 | Soltesz |
| 5,256,144 | A | 10/1993 | Kraus et al. |
| 5,257,974 | A | 11/1993 | Cox |
| 5,259,393 | A | 11/1993 | Corso, Jr. et al. |
| 5,267,979 | A | 12/1993 | Appling et al. |
| 5,267,982 | A | 12/1993 | Sylvanowicz |
| 5,279,562 | A | 1/1994 | Sirhan et al. |
| 5,284,128 | A | 2/1994 | Hart |
| 5,300,032 | A | 4/1994 | Hibbs et al. |
| 5,304,131 | A | 4/1994 | Paskar |
| 5,306,252 | A | 4/1994 | Yutori et al. |
| 5,308,435 | A | 5/1994 | Ruggles et al. |
| 5,315,906 | A | 5/1994 | Ferenczi et al. |
| 5,315,996 | A | 5/1994 | Lundquist |
| 5,318,529 | A | 6/1994 | Kontos |
| 5,322,064 | A | 6/1994 | Lundquist |
| 5,329,923 | A | 7/1994 | Lundquist |
| 5,333,620 | A | 8/1994 | Moutafis et al. |
| 5,334,145 | A | 8/1994 | Lundquist et al. |
| 5,336,205 | A | 8/1994 | Zenzen et al. |
| 5,341,818 | A | 8/1994 | Abrams et al. |
| 5,345,937 | A | 9/1994 | Middleman et al. |
| 5,345,945 | A | 9/1994 | Hodgson et al. |
| 5,354,623 | A | 10/1994 | Hall |
| 5,358,493 | A | 10/1994 | Schweich et al. |
| 5,358,796 | A | 10/1994 | Nakamura et al. |
| 5,365,942 | A | 11/1994 | Shank |
| 5,365,943 | A | 11/1994 | Jansen |
| 5,368,564 | A | 11/1994 | Savage |
| 5,368,661 | A | 11/1994 | Nakamura et al. |
| 5,376,084 | A | 12/1994 | Bacich et al. |
| 5,381,782 | A | 1/1995 | DeLaRama et al. |
| 5,406,960 | A | 4/1995 | Corso, Jr. |
| 5,411,476 | A | 5/1995 | Abrams |
| 5,425,723 | A | 6/1995 | Wang |
| 5,437,288 | A | 8/1995 | Schwartz et al. |
| 5,438,993 | A | 8/1995 | Lynch et al. |
| 5,439,000 | A | 8/1995 | Gunderson et al. |
| 5,441,483 | A | 8/1995 | Avitall |
| 5,441,489 | A | 8/1995 | Utsumi et al. |
| 5,447,812 | A | 9/1995 | Fukuda et al. |
| 5,454,787 | A | 10/1995 | Lundquist |
| 5,460,187 | A | 10/1995 | Daigle et al. |
| 5,470,330 | A | 11/1995 | Goldenberg et al. |
| 5,476,701 | A | 12/1995 | Berger |
| 5,477,856 | A | 12/1995 | Lundquist |
| 5,496,294 | A | 3/1996 | Hergenrother et al. |
| 5,497,785 | A | 3/1996 | Viera |
| 5,507,301 | A | 4/1996 | Wasicek et al. |
| 5,507,729 | A | 4/1996 | Lindenberg et al. |
| 5,507,751 | A | 4/1996 | Goode et al. |
| 5,507,766 | A | 4/1996 | Kugo et al. |
| 5,514,128 | A | 5/1996 | Hillsman et al. |
| 5,520,194 | A | 5/1996 | Miyata et al. |
| 5,520,645 | A | 5/1996 | Imran et al. |
| 5,531,719 | A | 7/1996 | Takahashi |
| 5,533,985 | A | 7/1996 | Wang |
| 5,546,958 | A | 8/1996 | Thorud et al. |
| 5,551,444 | A | 9/1996 | Finlayson |
| 5,554,139 | A | 9/1996 | Okajima |
| 5,562,619 | A | 10/1996 | Mirarchi et al. |
| 5,569,197 | A | 10/1996 | Helmus et al. |
| 5,569,200 | A | 10/1996 | Umeno et al. |
| 5,569,218 | A | 10/1996 | Berg |
| 5,571,073 | A | 11/1996 | Castillo |
| 5,573,520 | A | 11/1996 | Schwartz et al. |
| 5,584,821 | A | 12/1996 | Hobbs et al. |
| 5,599,326 | A | 2/1997 | Carter |
| 5,599,492 | A | 2/1997 | Engelson |
| 5,601,539 | A | 2/1997 | Corso, Jr. |
| 5,605,162 | A | 2/1997 | Mirzaee et al. |
| 5,622,184 | A | 4/1997 | Ashby et al. |
| 5,630,806 | A | 5/1997 | Inagaki et al. |

| | | |
|---|---|---|
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,833,672 A | 11/1998 | Kawata et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,902,499 A | 5/1999 | Richerzhagen |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,971,975 A | 10/1999 | Mills et al. |
| 5,980,471 A | 11/1999 | Jafari |
| 6,001,068 A | 12/1999 | Uchino et al. |
| 6,004,279 A | 12/1999 | Crowley et al. |
| 6,007,478 A | 12/1999 | Siess et al. |
| 6,014,919 A | 1/2000 | Jacobsen et al. |
| 6,017,319 A | 1/2000 | Jacobsen et al. |
| 6,022,341 A | 2/2000 | Lentz |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,090,099 A | 7/2000 | Samson et al. |
| 6,106,485 A | 8/2000 | McMahon |
| 6,106,488 A | 8/2000 | Fleming et al. |
| 6,135,992 A | 10/2000 | Wang |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B1 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,562,021 B1 | 5/2003 | Derbin et al. |
| 6,579,246 B2 | 6/2003 | Jacobsen et al. |
| 6,602,207 B1 | 8/2003 | Mam et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,648,024 B2 | 11/2003 | Wang |
| 6,652,508 B2 | 11/2003 | Griffin et al. |
| 6,663,614 B1 | 12/2003 | Carter |
| 6,682,493 B2 | 1/2004 | Mirigian |
| 6,689,120 B1 | 2/2004 | Gerdts |
| 6,702,762 B2 | 3/2004 | Jafari et al. |
| 6,702,802 B1 | 3/2004 | Hancock et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,939,593 B2 | 9/2005 | Wang |
| 6,953,470 B2 | 10/2005 | Holman et al. |
| 6,997,937 B2 | 2/2006 | Jacobsen et al. |
| 7,001,369 B2 | 2/2006 | Griffin et al. |
| 7,071,197 B2 | 7/2006 | Leonardi et al. |
| 7,074,197 B2 | 7/2006 | Reynolds et al. |
| 7,153,277 B2 | 12/2006 | Skujins et al. |
| 7,153,320 B2 | 12/2006 | Euteneuer et al. |
| 7,166,099 B2 | 1/2007 | Devens, Jr. |

| | | | | | | |
|---|---|---|---|---|---|---|
| 7,169,118 B2 | 1/2007 | Reynolds et al. | | JP | 62-089470 | 4/1987 |
| 7,182,735 B2 | 2/2007 | Shireman et al. | | JP | 62-299277 | 12/1987 |
| RE39,668 E | 5/2007 | Bagaoisan et al. | | JP | 63-93516 | 4/1988 |
| 2002/0013540 A1 | 1/2002 | Jacobsen et al. | | JP | 63-181774 | 7/1988 |
| 2002/0019599 A1 | 2/2002 | Rooney et al. | | JP | 63-217966 | 9/1988 |
| 2003/0009208 A1 | 1/2003 | Snyder et al. | | JP | 10-89956 | 4/1989 |
| 2003/0060732 A1 | 3/2003 | Jacobsen et al. | | JP | 1-135363 | 5/1989 |
| 2003/0069522 A1 | 4/2003 | Jacobsen et al. | | JP | 1-158936 | 6/1989 |
| 2003/0216668 A1 | 11/2003 | Howland et al. | | JP | 2-107268 | 4/1990 |
| 2004/0030266 A1* | 2/2004 | Murayama et al. ........... 600/585 | | JP | 03-122850 | 12/1991 |
| 2004/0116831 A1 | 6/2004 | Vrba | | JP | 4-061840 | 2/1992 |
| 2004/0142643 A1 | 7/2004 | Miller et al. | | JP | 4-099963 | 3/1992 |
| 2004/0167436 A1 | 8/2004 | Reynolds et al. | | JP | 4-213069 | 8/1992 |
| 2004/0167437 A1 | 8/2004 | Sharrow et al. | | JP | 4-213070 | 8/1992 |
| 2004/0167441 A1 | 8/2004 | Reynolds et al. | | JP | 4-236965 | 8/1992 |
| 2004/0181174 A2 | 9/2004 | Davis et al. | | JP | 5-149969 | 6/1993 |
| 2004/0181176 A1 | 9/2004 | Jafari et al. | | JP | 5-506806 | 10/1993 |
| 2005/0004523 A1 | 1/2005 | Osborne et al. | | JP | 5-309519 | 11/1993 |
| 2005/0027212 A1* | 2/2005 | Segner et al. ................ 600/585 | | JP | 5-507857 | 11/1993 |
| 2005/0115624 A1 | 6/2005 | Walak | | JP | 6-501179 | 2/1994 |
| 2006/0027009 A1 | 2/2006 | Martin et al. | | JP | 6-31749 | 4/1994 |
| 2006/0121218 A1 | 6/2006 | Obara et al. | | JP | 6-169996 | 6/1994 |
| 2006/0122537 A1 | 6/2006 | Reynolds et al. | | JP | 6-63224 | 9/1994 |
| 2006/0189896 A1 | 8/2006 | Davis et al. | | JP | 6-312313 | 11/1994 |
| 2006/0264904 A1 | 11/2006 | Kerby et al. | | JP | 7-28562 | 5/1995 |
| 2007/0049846 A1* | 3/2007 | Bown et al. ................... 600/585 | | JP | 7-124164 | 5/1995 |
| 2007/0100285 A1 | 5/2007 | Griffin et al. | | JP | 7-124263 | 5/1995 |
| 2007/0100424 A1 | 5/2007 | Chew et al. | | JP | 7-136280 | 5/1995 |
| 2007/0232957 A1* | 10/2007 | Murayama et al. ........... 600/585 | | JP | 7-148264 | 6/1995 |
| 2008/0021347 A1 | 1/2008 | Jacobsen et al. | | JP | 7-505561 | 6/1995 |
| 2008/0021348 A1 | 1/2008 | Jacobsen et al. | | JP | 7-37199 | 7/1995 |
| 2008/0021400 A1 | 1/2008 | Jacobsen et al. | | JP | 7-185009 | 7/1995 |
| 2008/0021401 A1 | 1/2008 | Jacobsen et al. | | JP | 7-255855 | 10/1995 |
| 2008/0021402 A1 | 1/2008 | Jacobsen et al. | | JP | 7-275366 | 10/1995 |
| 2008/0021403 A1 | 1/2008 | Jacobsen et al. | | JP | 7-51067 | 11/1995 |
| 2008/0021404 A1 | 1/2008 | Jacobsen et al. | | JP | 8-229888 | 9/1996 |
| 2008/0021405 A1 | 1/2008 | Jacobsen et al. | | JP | 8-509141 | 10/1996 |
| 2008/0021406 A1 | 1/2008 | Jacobsen et al. | | JP | 8-317988 | 12/1996 |
| 2008/0021407 A1 | 1/2008 | Jacobsen et al. | | JP | 9-000164 | 4/1997 |
| 2008/0021408 A1 | 1/2008 | Jacobsen et al. | | JP | 9-276413 | 10/1997 |
| 2008/0077119 A1 | 3/2008 | Snyder et al. | | JP | 9-294813 A | 11/1997 |
| 2008/0200839 A1* | 8/2008 | Bunch et al. ................. 600/585 | | JP | 10-118193 | 5/1998 |
| 2009/0043283 A1 | 2/2009 | Turnlund et al. | | JP | 10-328191 | 12/1998 |
| | | | | JP | 11-267224 A | 10/1999 |
| FOREIGN PATENT DOCUMENTS | | | | JP | 2000-197704 A | 7/2000 |
| BR | PI 9712829 | 1/2000 | | JP | 2000-510722 A | 8/2000 |
| CA | 2266685 | 5/2006 | | JP | 2000-511083 A | 8/2000 |
| CA | 2255781 | 3/2007 | | JP | 3081831 | 8/2000 |
| CN | 1230914 | 10/1999 | | JP | 2001-500808 A | 1/2001 |
| DE | 285514 | 12/1990 | | JP | 2002-529137 A | 9/2002 |
| EP | 0 045 931 | 2/1982 | | JP | 3325828 | 9/2002 |
| EP | 0 069 522 | 1/1983 | | JP | 2002-542901 A | 12/2002 |
| EP | 0 087 933 | 9/1983 | | JP | 2002-543896 A | 12/2002 |
| EP | 0 111 044 | 6/1984 | | JP | 2003-517893 A | 6/2003 |
| EP | 0 181 174 | 5/1986 | | JP | 3649604 | 5/2005 |
| EP | 0 215 173 | 3/1987 | | JP | 2005-534407 | 11/2005 |
| EP | 0317905 | 5/1989 | | SU | 712908 | 1/1980 |
| EP | 0 377 453 | 7/1990 | | SU | 758421 | 8/1980 |
| EP | 0 565 065 | 6/1996 | | SU | 1529365 | 12/1989 |
| EP | 0 778 039 | 6/1997 | | WO | WO 90/02520 | 3/1990 |
| EP | 0 778 040 | 6/1997 | | WO | WO 91/13364 | 9/1991 |
| EP | 0 865 772 | 9/1998 | | WO | WO 92/04072 | 3/1992 |
| EP | 0 865 773 | 9/1998 | | WO | WO 92/07619 | 5/1992 |
| EP | 0 521 595 | 5/1999 | | WO | WO 93/04722 | 3/1993 |
| EP | 0 917 885 | 8/1999 | | WO | WO 93/11313 | 6/1993 |
| EP | 0 790 066 | 4/2000 | | WO | WO 95/24236 | 9/1995 |
| EP | 0 812 599 | 8/2002 | | WO | WO 95/32834 | 12/1995 |
| EP | 0 608 853 | 4/2003 | | WO | WO 96/19255 | 6/1996 |
| EP | 0 935 947 | 12/2004 | | WO | WO 96/38193 | 12/1996 |
| EP | 0 937 481 | 4/2005 | | WO | WO 97/10022 | 3/1997 |
| EP | 0 934 141 | 11/2005 | | WO | WO 97/25914 | 7/1997 |
| EP | 0 778 038 | 6/2006 | | WO | WO 97/43949 | 11/1997 |
| GB | 2130885 | 6/1984 | | WO | WO 97/44083 | 11/1997 |
| GB | 2214354 | 8/1989 | | WO | WO 97/44086 | 11/1997 |
| GB | 2257269 | 1/1993 | | WO | WO 98/10694 | 3/1998 |
| JP | 58-8522 | 1/1983 | | WO | WO 99/04847 | 2/1999 |
| JP | 60-091858 | 5/1985 | | WO | WO 99/11313 | 3/1999 |
| JP | 61-022752 | 1/1986 | | WO | WO 00/27303 | 5/2000 |
| JP | 62-023361 | 1/1987 | | WO | WO 00/30710 | 6/2000 |

| | | | | | | |
|---|---|---|---|---|---|---|
| WO | WO 00/48645 | 8/2000 | | WO | WO 02/062540 | 8/2002 |
| WO | WO 00/57943 | 10/2000 | | WO | WO 03/004086 | 1/2003 |
| WO | WO 00/66199 | 11/2000 | | WO | WO 03/008148 | 1/2003 |
| WO | WO 00/67845 | 11/2000 | | WO | WO 03/041783 | 5/2003 |
| WO | WO 00/72907 | 12/2000 | | WO | WO 2004/012804 | 2/2004 |
| WO | WO 01/28620 | 4/2001 | | WO | WO 2004/047899 | 6/2004 |
| WO | WO 01/36034 | 5/2001 | | WO | WO 2007/050718 | 5/2007 |
| WO | WO 01/45773 | 6/2001 | | WO | WO 2008/034010 | 3/2008 |
| WO | WO 01/45912 | 6/2001 | | | | |
| WO | WO 01/93920 | 12/2001 | | | | |
| WO | WO 02/13682 | 2/2002 | | | | |

* cited by examiner

MEDICAL DEVICES AND TAPERED TUBULAR MEMBERS FOR USE IN MEDICAL DEVICES

FIELD OF THE INVENTION

The present invention pertains to medical devices, and methods for manufacturing medical devices. More particularly, the present invention pertains to elongated intracorporal medical devices including a slotted tubular member.

BACKGROUND

A wide variety of intracorporal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include a metallic tubular member including a tube wall defining an inner diameter and having a wall thickness. The tubular member may have a plurality of slots formed therein. The tubular member may also include first portion having a first length. The tube wall may have a substantially constant wall thickness across the first length. The tubular member may also include a second portion having a second length. The tube wall may thin so that the inner diameter increases across the second length.

An example guidewire may include a metallic tubular member having a tube wall, an outer diameter, and a distal end region. The distal end region may have a thinned length. The tube wall may thin so that the outer diameter decreases across the thinned length. The tubular member may have a plurality of slots formed therein. A tip member may be attached to the distal end region. The tip member may overlap with the thinned length.

Another example guidewire may include a metallic tubular member having a tube wall, an inner diameter, and a distal end region. The distal end region may have a thinned length. The tube wall may thin so that the inner diameter increases across the thinned length. The tubular member may have a plurality of slots formed therein. A tip member may be attached to the distal end region. The tip member may overlap with the thinned length.

Another example medical device may include a metallic tubular member including a distal end. The tubular member may include a tube wall having an inner surface and an outer surface. At the distal end of the tubular member, the inner surface and the outer surface may taper to thin the tube wall.

An example method for manufacturing a medical device may include providing a metallic tubular member including a tube wall defining an inner diameter, forming a plurality of slots in the tubular member, and thinning a portion of the tube wall. Along the portion of the tube wall that is thinned the inner diameter may be increased.

BRIEF DESCRIPTION OF THE DRAWINGS

The invention may be more completely understood in consideration of the following detailed description of various embodiments of the invention in connection with the accompanying drawings, in which.

Figure 1:
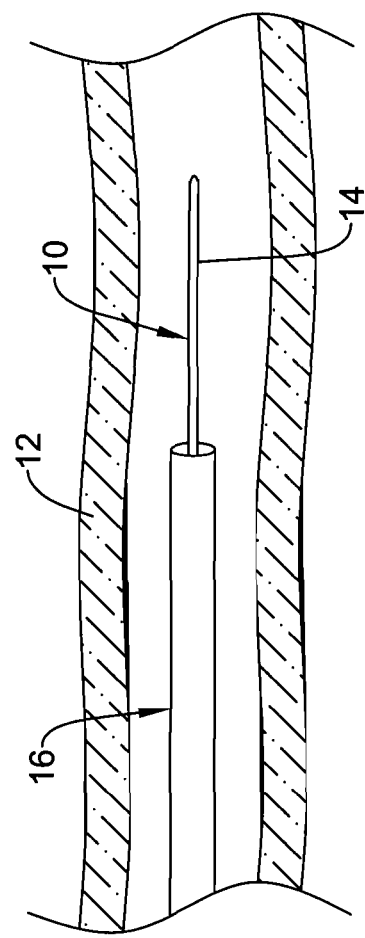
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for use within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Although medical device 10 is depicted in several of the drawings as a guidewire, it is not intended to be limited to just being a guidewire. Indeed, medical device 10 may take the form of any suitable guiding, diagnosing, or treating device (including catheters, endoscopic instruments and/or endoscopes, laparoscopic instruments, stent delivery systems, embolic filter systems, urology stone retrieval systems, embolic coil delivery systems, atherectomy shafts, thermoctomy shafts, etc., and the like) and it may be suitable for use at essentially any location and/or body lumen within a patient. For example, medical device/guidewire 10 may be suitable for use in neurological interventions, coronary interventions, peripheral interventions, etc. As such, guidewire 10 may be appropriately sized for any given intervention. For example, guidewire 10 may have an outside diameter of about 0.001 to 0.5 inches or about 0.0015 to 0.05 inches (e.g., about 0.010 to 0.014 inches) for neurological interventions; an outside diameter of about 0.001 to 0.5 inches or about 0.01 to 0.05 inches (e.g., about 0.014 inches) for coronary interventions; or an outside diameter of about 0.01 to 0.5 inches or about 0.02 to 0.05 inches (e.g., about 0.014 to 0.038 inches) for peripheral interventions. These dimensions, of course, may vary depending on, for example, the type of device (e.g., catheter, guidewire, etc.), the anatomy of the patient, and/or the goal of the intervention. In at least some embodiments, for example, guidewire 10 may be a crossing guidewire that can be used to help a clinician cross an occlusion or stenosis in vessel 12.

Figure 2:
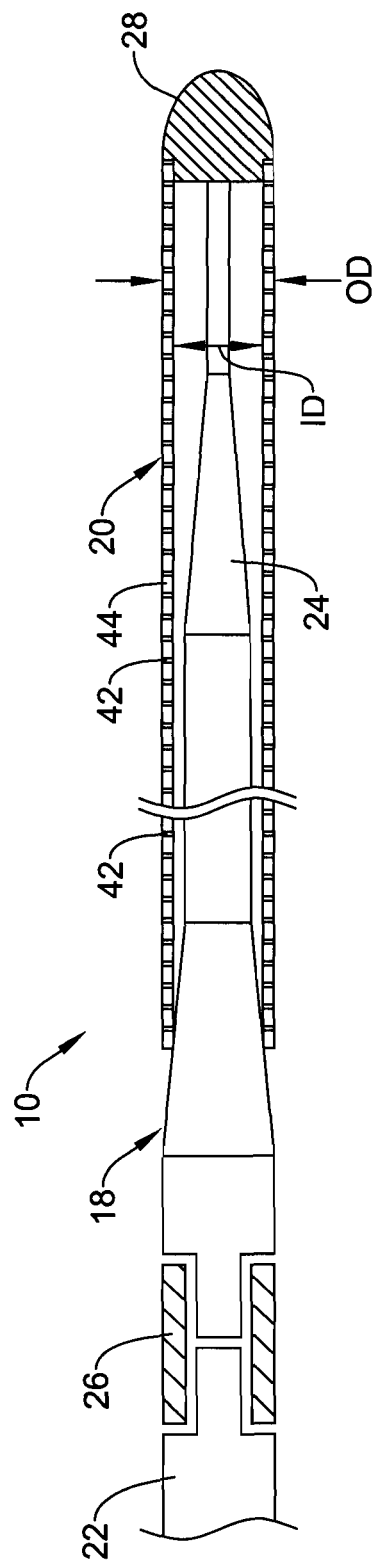
FIG. 2 is a partial cross-sectional view of an example medical device.
Figure 3:
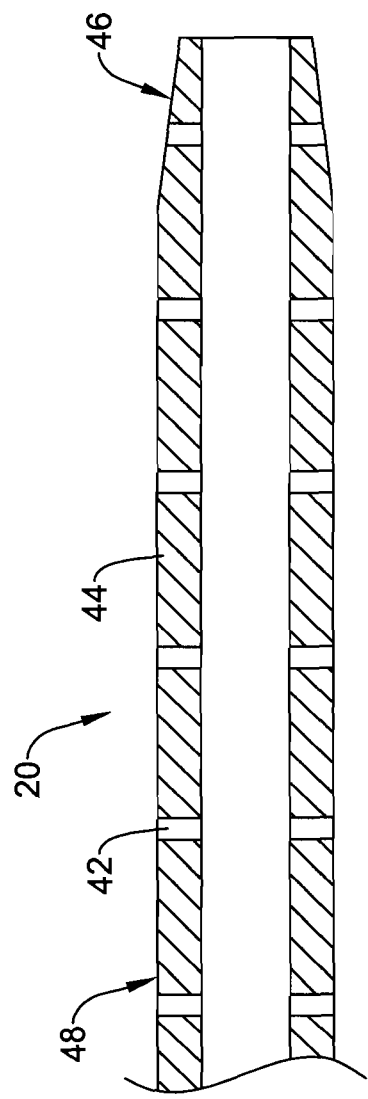
FIG. 3 is a cross-sectional side view of an example tubular member.

FIG. 2 is a partial cross-sectional view of guidewire 10. Here it can be seen that guidewire 10 may include a core member or core wire 18 and a tubular member 20 disposed over at least a portion of core wire 18. Core wire 18 may include a proximal section 22 and a distal section 24. A connector 26 may couple or otherwise attach proximal section 22 to distal section 24. Alternatively, core wire 18 may be a unitary member without a connector. A tip member 28 may also be coupled to core wire 18 and/or tubular member 20 that may define an atraumatic distal tip of guidewire 10. In at least some embodiments, tip member 28 may include a solder ball tip. Alternatively, tip member 28 may include a polymeric material. A coil (not shown) may be disposed in tubular member 20, for example adjacent tip member 28. In at least some embodiments, the coil may take the form of a radiopaque coil.

In at least some embodiments, tubular member 20 includes a plurality of cuts, apertures, and/or slots 42 formed therein.

Various embodiments of arrangements and configurations of slots 42 are contemplated. In some embodiments, at least some, if not all of slots 42 are disposed at the same or a similar angle with respect to the longitudinal axis of the tubular member 20. As shown, slots 42 can be disposed at an angle that is perpendicular, or substantially perpendicular, and/or can be characterized as being disposed in a plane that is normal to the longitudinal axis of tubular member 20. However, in other embodiments, slots 42 can be disposed at an angle that is not perpendicular, and/or can be characterized as being disposed in a plane that is not normal to the longitudinal axis of tubular member 20. Additionally, a group of one or more slots 42 may be disposed at different angles relative to another group of one or more slots 42. The distribution and/or configuration of slots 42 can also include, to the extent applicable, any of those disclosed in U.S. Pat. Publication No. US 2004/0181174, the entire disclosure of which is herein incorporated by reference.

Slots 42 may be provided to enhance the flexibility of tubular member 20 while still allowing for suitable torque transmission characteristics. Slots 42 may be formed such that one or more rings and/or turns interconnected by one or more segments and/or beams are formed in tubular member 20, and such rings and beams may include portions of tubular member 20 that remain after slots 42 are formed in the body of tubular member 20. Such an interconnected ring structure may act to maintain a relatively high degree of tortional stiffness, while maintaining a desired level of lateral flexibility. In some embodiments, some adjacent slots 42 can be formed such that they include portions that overlap with each other about the circumference of tubular member 20. In other embodiments, some adjacent slots 42 can be disposed such that they do not necessarily overlap with each other, but are disposed in a pattern that provides the desired degree of lateral flexibility.

Additionally, slots 42 can be arranged along the length of, or about the circumference of, tubular member 20 to achieve desired properties. For example, adjacent slots 42, or groups of slots 42, can be arranged in a symmetrical pattern, such as being disposed essentially equally on opposite sides about the circumference of tubular member 20, or can be rotated by an angle relative to each other about the axis of tubular member 20. Additionally, adjacent slots 42, or groups of slots 42, may be equally spaced along the length of tubular member 20, or can be arranged in an increasing or decreasing density pattern, or can be arranged in a non-symmetric or irregular pattern. Other characteristics, such as slot size, slot shape and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section 26, or a distal section 28, or the entire tubular member 20, may not include any such slots 42.

As suggested above, slots 42 may be formed in groups of two, three, four, five, or more slots 42, which may be located at substantially the same location along the axis of tubular member 20. Within the groups of slots 42, there may be included slots 42 that are equal in size (i.e., span the same circumferential distance around tubular member 20). In some of these as well as other embodiments, at least some slots 42 in a group are unequal in size (i.e., span a different circumferential distance around tubular member 20). Longitudinally adjacent groups of slots 42 may have the same or different configurations. For example, some embodiments of tubular member 20 include slots 42 that are equal in size in a first group and then unequally sized in an adjacent group. It can be appreciated that in groups that have two slots 42 that are equal in size, the beams (i.e., the portion of tubular member 20 remaining after slots 42 are formed therein) are aligned with the center of tubular member 20. Conversely, in groups that have two slots 42 that are unequal in size, the beams are offset from the center of tubular member 20. Some embodiments of tubular member 20 include only slots 42 that are aligned with the center of tubular member 20, only slots 42 that are offset from the center of tubular member 20, or slots 42 that are aligned with the center of tubular member 20 in a first group and offset from the center of tubular member 20 in another group. The amount of offset may vary depending on the depth (or length) of slots 42 and can include essentially any suitable distance.

Slots 42 can be formed by methods such as micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 20 is formed by cutting and/or removing portions of the tube to form slots 42. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 42 in tubular member 20 using any of these or other manufacturing steps.

In at least some embodiments, slots 42 may be formed in tubular member using a laser cutting process. The laser cutting process may include essentially any suitable laser and/or laser cutting apparatus. For example, the laser cutting process may utilize a fiber laser. Utilizing processes like laser cutting may be desirable for a number of reasons. For example, laser cutting processes may allow tubular member 20 to be cut into a number of different cutting patterns in a precisely controlled manner. This may include variations in the slot width (which also may be termed "kerf"), ring width, beam height and/or width, etc. Furthermore, changes to the cutting pattern can be made without the need to replace the cutting instrument (e.g., a blade). This may also allow smaller tubes (e.g., having a smaller outer diameter) to be used to form tubular member 20 without being limited by a minimum cutting blade size. Consequently, tubular members 20 may be fabricated for use in neurological devices or other devices where a small size may be desired.

As indicated above, slots 42 may be useful in that they may add desirable flexibility characteristics to tubular member 20. Tubular member 20 may also (or alternatively) include one or more additional structural features that desirably impact the flexibility characteristics. For example, tubular member 20 may include a tube wall 44 that defines an inner diameter ID and an outer diameter OD and, in at least some embodiments, tubular member 20 may include a region where tube wall 44 thins so that the inner diameter, the outer diameter, or both vary along the length of tubular member 20. Those portions of tubular member 20 that bear a thinned tube wall 44 may have increased flexibility. Because of this, these portions may be disposed at a desirable location in guidewire 10. For example, it may be desirable for the portions of tubular member 20 having a thinned tube wall 44 to be disposed adjacent joints or transitions, near the distal end or tip, adjacent other structures that may be more stiff or less flexible, or at any other suitable location along guidewire 10. Analogously, other structures of guidewire 10 may also be thinned in a similar way to provide desirable flexibility characteristics. Additionally, other medical devices and/or medical device components including, for example, coils, polymer sleeves, tips of balloons, the ends of stents, and the like may also be thinned to provide desirable flexibility characteristics.

FIGS. 3-14 illustrate examples of how some of the variations in inner diameter, outer diameter, or both may manifest for guidewire 10 or other suitable devices. For simplicity purposes, FIGS. 3-14 utilize like reference numbers. However, a number of different embodiments of tubular member 20 are contemplated that include any one or more of the configurations illustrated in FIGS. 3-14. In addition, FIGS. 3-14 illustrate that the portions of tubular member 20 having a thinned tube wall 44 are disposed at an end (e.g., the distal end) of tubular member 20. This, however, is not intended to limit the invention as numerous tubular members 20 are contemplated where the portions having a thinned tube wall 44 are located at any position along the length of tubular member 20.

Figure 4:
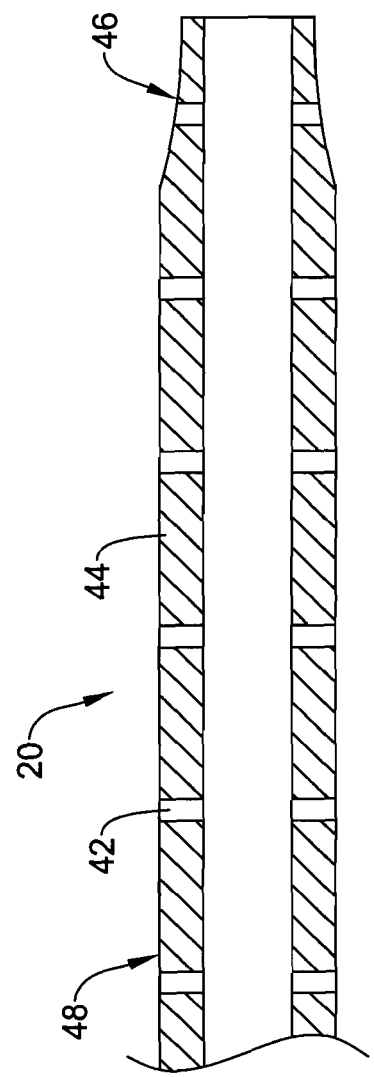
FIG. 4 is a cross-sectional side view of another example tubular member.
Figure 5:
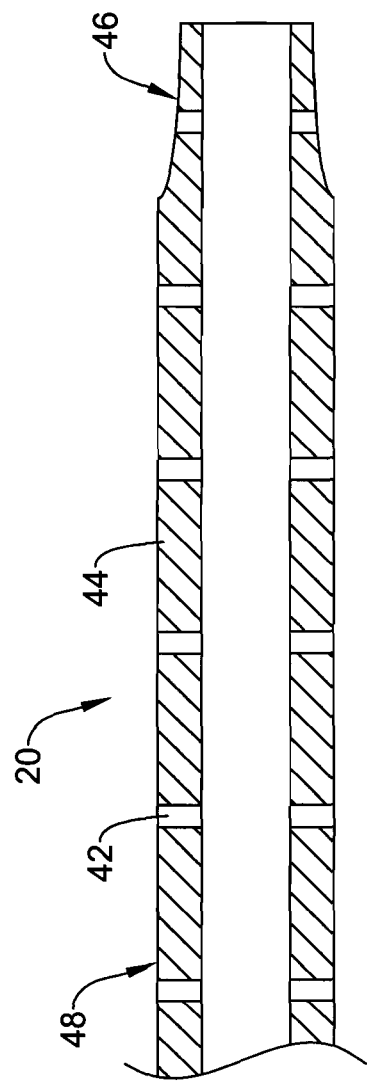
FIG. 5 is a cross-sectional side view of another example tubular member.
Figure 6:
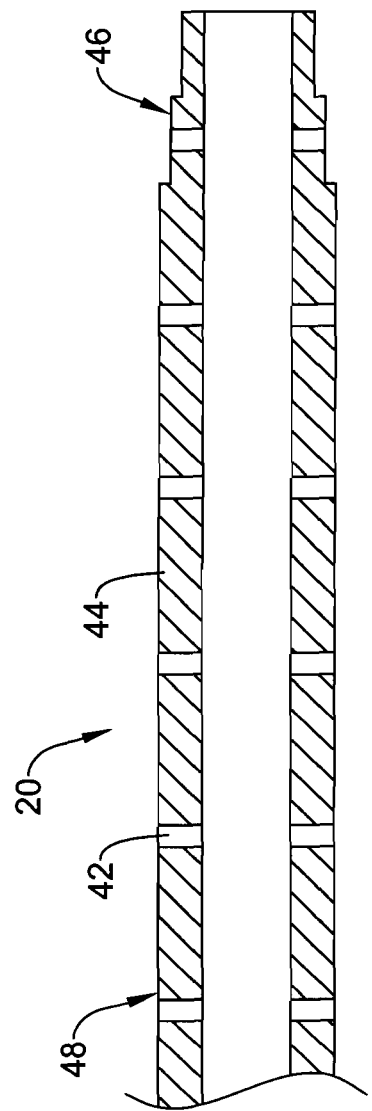
FIG. 6 is a cross-sectional side view of another example tubular member.
Figure 7:
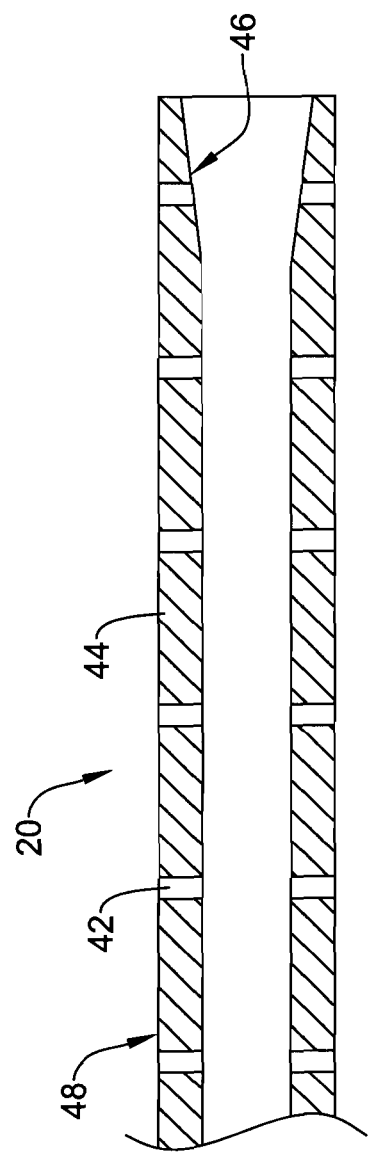
FIG. 7 is a cross-sectional side view of another example tubular member.

Referring now to FIGS. 3-6, these figures illustrate example tubular members 20 that include a region 46 where the outer diameter OD varies. In these embodiments, tube wall 44 thins along the exterior of tubular member 20. For example, in FIG. 3, tube wall 44 thins in a linear manner along region 46 of tubular member 20. In FIG. 4, tube wall 44 thins in a curved manner along region 46 of tubular member 20. In FIG. 5, tube wall 44 thins in a parabolic manner along region 46 of tubular member 20. In FIG. 6, tube wall 44 thins in a stepped manner along region 46 of tubular member 20. These tubular members 20 may also include a region 48 where both the inner diameter ID and the outer diameter OD remains substantially constant.

Figure 8:
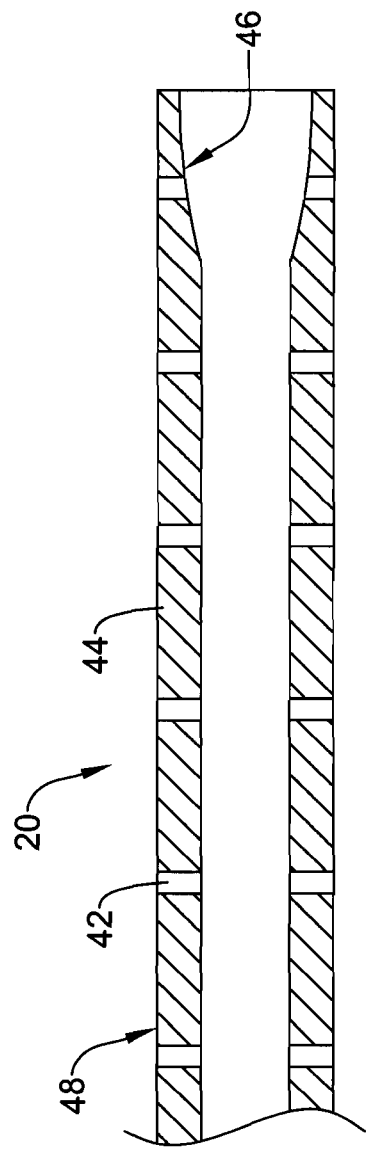
FIG. 8 is a cross-sectional side view of another example tubular member.
Figure 9:
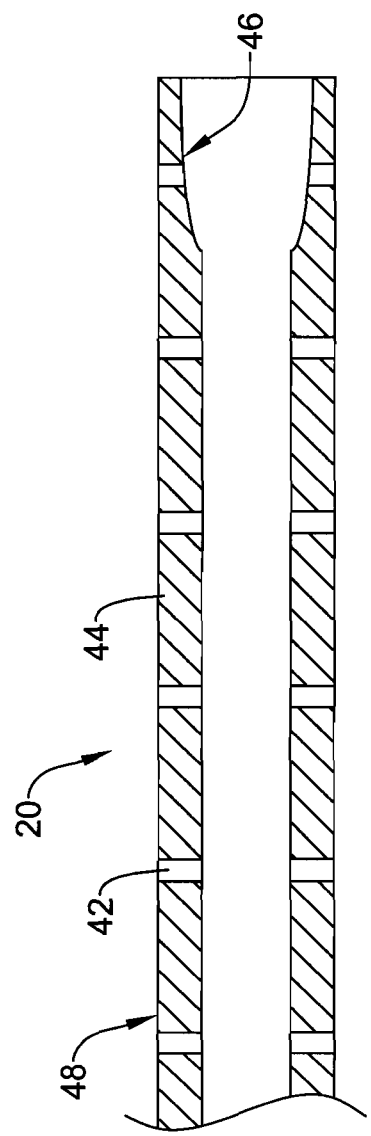
FIG. 9 is a cross-sectional side view of another example tubular member.
Figure 10:
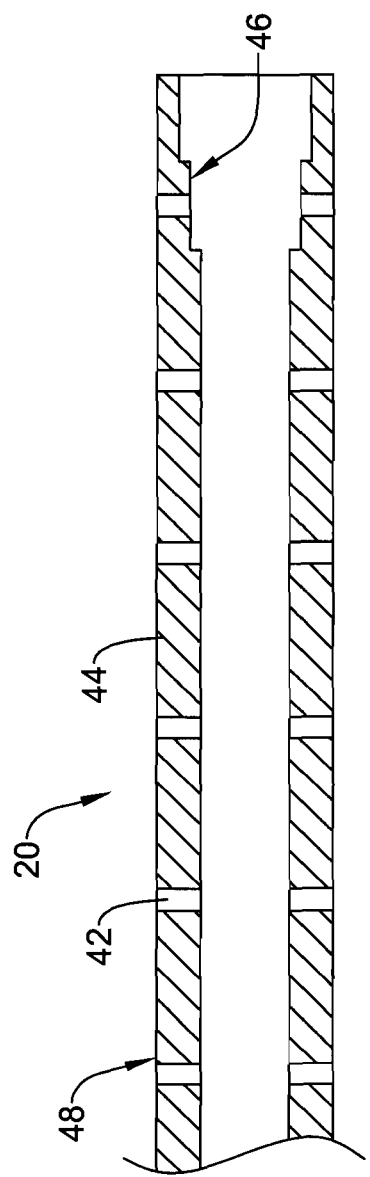
FIG. 10 is a cross-sectional side view of another example tubular member.
Figure 11:
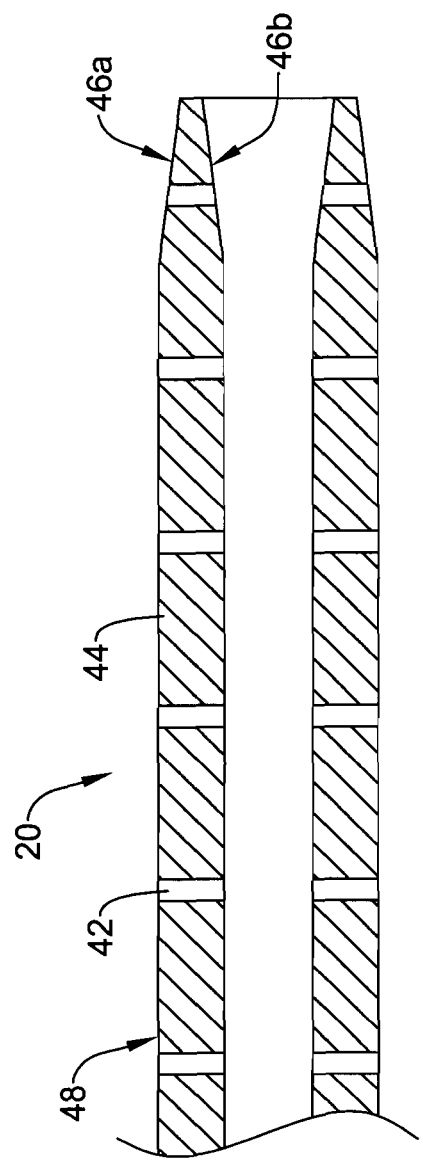
FIG. 11 is a cross-sectional side view of another example tubular member.

Likewise, FIGS. 7-10 illustrate example tubular members 20 that include a region 46 where the inner diameter ID varies. In these embodiments, tube wall 44 thins along the interior of tubular member 20. For example, in FIG. 7, tube wall 44 thins in a linear manner along region 46 of tubular member 20. In FIG. 8, tube wall 44 thins in a curved manner along region 46 of tubular member 20. In FIG. 9, tube wall 44 thins in a parabolic manner along region 46 of tubular member 20. In FIG. 10, tube wall 44 thins in a stepped manner along region 46 of tubular member 20. These tubular members 20 may also include a region 48 where both the inner diameter ID and the outer diameter OD remains substantially constant.

Figure 12:
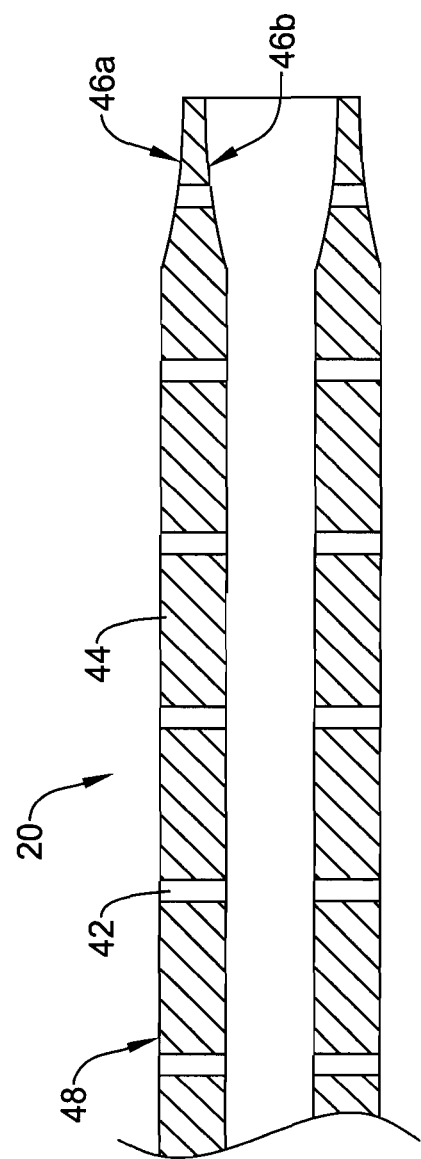
FIG. 12 is a cross-sectional side view of another example tubular member.
Figure 13:
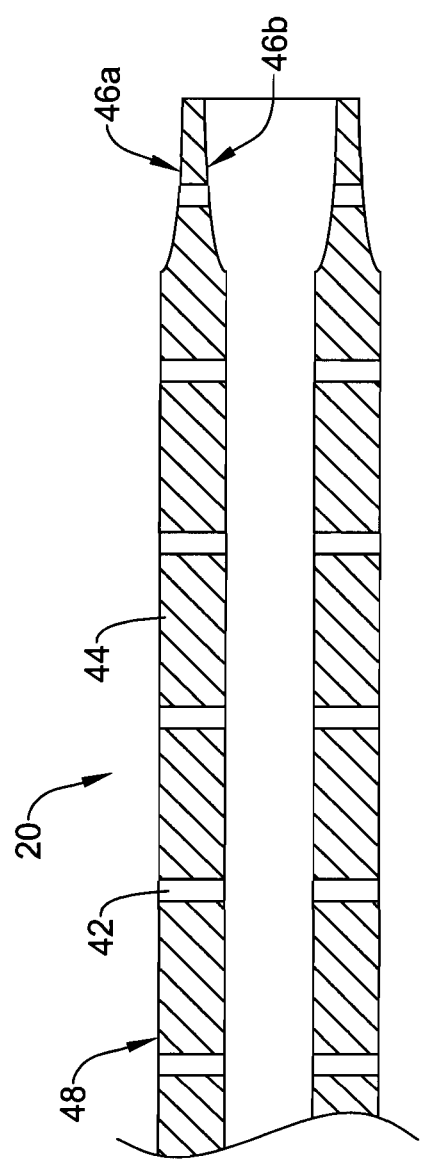
FIG. 13 is a cross-sectional side view of another example tubular member.
Figure 14:
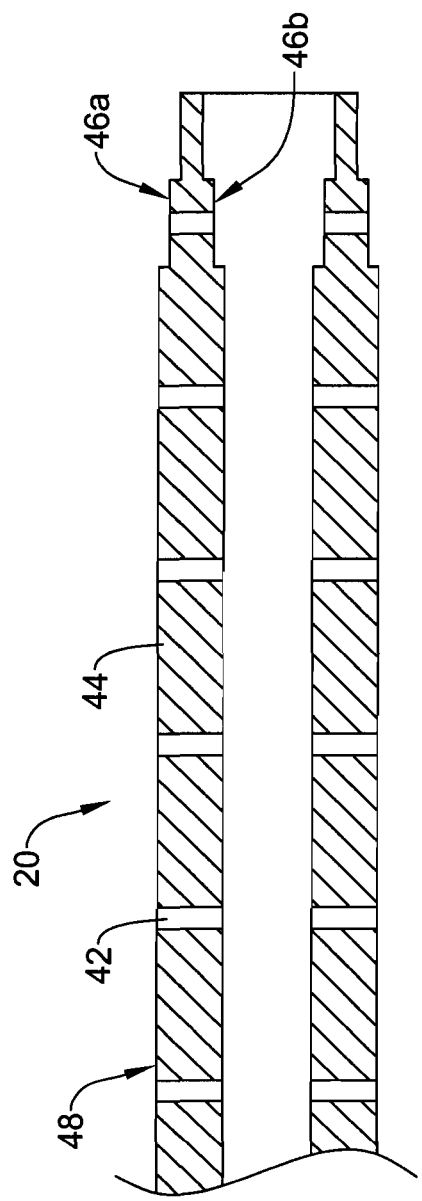
FIG. 14 is a cross-sectional side view of another example tubular member.

Moreover, FIGS. 11-14 illustrate example tubular members 20 that include a region 46 where both the inner diameter ID and the outer diameter OD vary. In these embodiments, tube wall 44 thins along both the interior and the exterior of tubular member 20. For example, in FIG. 11, tube wall 44 thins in a linear manner along region 46a (e.g., along the exterior) and region 46b (e.g., along the interior) of tubular member 20. In FIG. 12, tube wall 44 thins in a curved manner along 46a (e.g., along the exterior) and region 46b (e.g., along the interior) of tubular member 20. In FIG. 13, tube wall 44 thins in a parabolic manner along 46a (e.g., along the exterior) and region 46b (e.g., along the interior) of tubular member 20. In FIG. 14, tube wall 44 thins in a stepped manner along 46a (e.g., along the exterior) and region 46b (e.g., along the interior) of tubular member 20. These tubular members 20 may also include a region 48 where both the inner diameter ID and the outer diameter OD remains substantially constant. It should be noted that although regions 46a/46b in FIGS. 11-14 are illustrated such that tube wall 44 thins in the same manner along both the interior and the exterior of tubular member 20, this is not intended to be limiting. Indeed, tubular members 20 are contemplated where tube wall 44 thins along the interior and the exterior in different manners (e.g., linear and parabolic, curved and stepped, etc.).

For the above discussion, tube wall 44 thinning in a "linear" manner may be understood to mean that tube wall 44 thins at a substantially constant rate or along a substantially constant slope over a particular distance. Tube wall 44 thinning in a "curved" manner may be understood to mean that tube wall 44 thins at a constantly changing rate, or along a constantly changing slope (e.g., increasing, decreasing, or both), or along a shape that is curved over a particular distance. Tube wall 44 thinning in a "parabolic" manner may be understood to mean that tube wall 44 thins at a changing rate or along a changing slope (e.g., increasing, decreasing, or both), or along a shape that is parabolic over a particular distance. Tube wall 44 thinning in a "stepped" manner may be understood to mean that tube wall 44 thins along a series of one or more steps in wall thickness over a particular distance.

The above discussion indicates that tube wall 44 may be thinned in a linear manner, a curved manner, a parabolic manner, or a stepped manner. These specific manners of thinning tube wall 44 are not intended to limit the invention as tube wall 44 may be thinned in any suitable manner. Consequently, tube wall 44 may be thinned in a way that can be described by essentially any suitable mathematical equation, in any regular or irregular manner, randomly, or in any other suitable way.

In general, the thinning of tube wall 44 may increase the flexibility of tubular member 20 by reducing the moment of inertia. The moment of inertia about the axis of a round component is $I=(\Pi/4)(radius)^4$. Similarly, the moment of inertia about the axis of a round tubular component (e.g., tubular member 20) is $I=(\Pi/4)(R_{OD}^4-R_{ID}^4)$, where $R_{OD}$ is the radius of the outer dimension of the tube and $R_{ID}$ is the radius of the inner dimension of the tube. Thus, as the radius of tubular member 20 varies, the moment of inertia changes by the fourth power of the radius. Based on this relationship, the outer diameter OD and/or the inner diameter ID can be selected so as to provide tubular member with the desired flexibility characteristics. Moreover, by altering the moment of inertia to the desired extent, tubular member 20 can be fabricated with a "custom" or specially-tailored flexibility characteristics.

Thinning tube wall 44 may be accomplished in a number of different manners. The appropriate manner for thinning tube wall 44 may depend on the material utilized for tubular member. For example, embodiments of tubular member 20 that are made from a polymer may be molded, cast, extruded, or otherwise formed into the desired shape. In embodiments where a metal is utilized, some of these or similar methods may be used. Additionally, other techniques may also be utilized including, for example, grinding (e.g., centerless grinding, end-grinding, plunge grinding, OD grinding, etc.), chemical etching, metal forming, or the like may also be utilized.

Fabricating a tubular member that is appropriately sized for use in guidewire 10 and has the appropriately thinned tube wall 44 may prove challenging, particularly when tubular member 20 is made from a shape-memory and/or super-elastic material (e.g., shape-memory and/or super-elastic nickel-titanium alloy) where the desirable shape-memory and/or super-elastic properties may be altered by using shaping techniques such as molding, casting, etc. Because of this, it may be necessary in some instances to utilize a more mechanical technique to thin tube wall 44. Additionally, thinning tube wall 44 along the exterior of tubular member 20 may be accomplished used relatively convention grinding (e.g., conventional centerless grinding) techniques. However, conventional grinding may not be suitable for thinning tube wall 44 along the interior of tubular member 20. Therefore, it may be necessary to formulate an alternative method for thinning tube wall 44 along the interior of tubular member 20. In some embodiments, tube wall 44 can be thinned by fabricating a tool having an exterior corresponding to the desired final shape for tubular member 20 along it interior and then using the tool to bore out or otherwise shape tubular member 20 in the desired manner. Other suitable techniques may also be utilized without departing from the spirit of the invention.

As indicated above, thinning tube wall 44 may desirable impact the flexibility characteristics of tubular member 20. Because of this, the thinned portions of tube wall 44 may be disposed at a desired location including, for example, the distal tip of guidewire 10, adjacent a transition in materials and/or components, or at any other suitable location.

Figure 15:
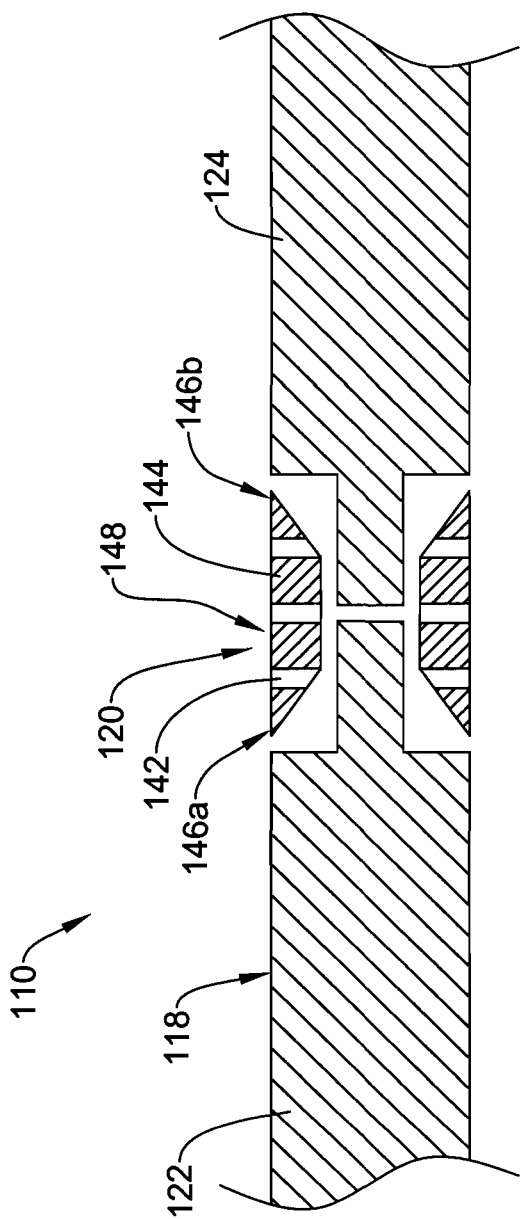
FIG. 15 is a cross-sectional side view of a portion of another example medical device.

FIG. 15 illustrates a portion of another example medical device 110 that includes core wire 118 and tubular member 120. In this embodiment, tubular member 120 may include slots 142 and tubular member 120 may function as a connector (similar to connector 26) that joins together proximal core portion 122 and distal core portion 124. Just like a number of the tubular members disclosed herein, tubular member 120 may include a portion 148 having a substantially constant inner and outer diameter and tubular member 120 may include one or more portions 146a/146b (e.g., disposed at the ends of tubular member 120) where tube wall 144 thins. This embodiment illustrates that thinned portions 146a/146b may be utilized at any portion of tubular member 120 including the proximal end and distal end. Furthermore, because tubular member 120 may be disposed a distal proximally of the distal end of device 110, this embodiment illustrates that thinned portions 146a/146b need not be disposed at the distal end or distal most portion of device 110.

Figure 16:
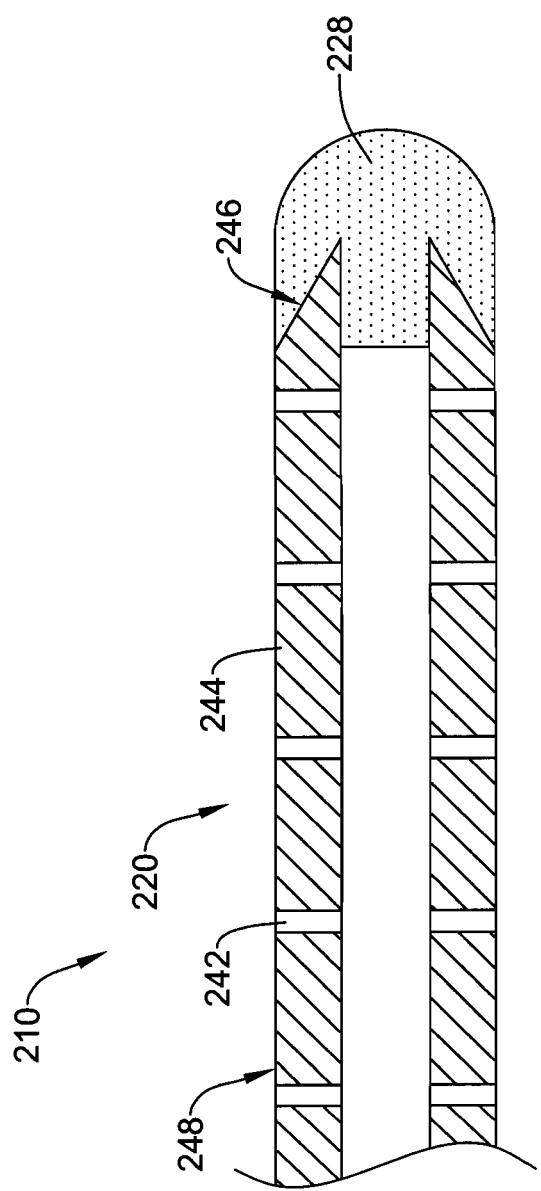
FIG. 16 is a cross-sectional side view of a portion of another example medical device.
Figure 17:
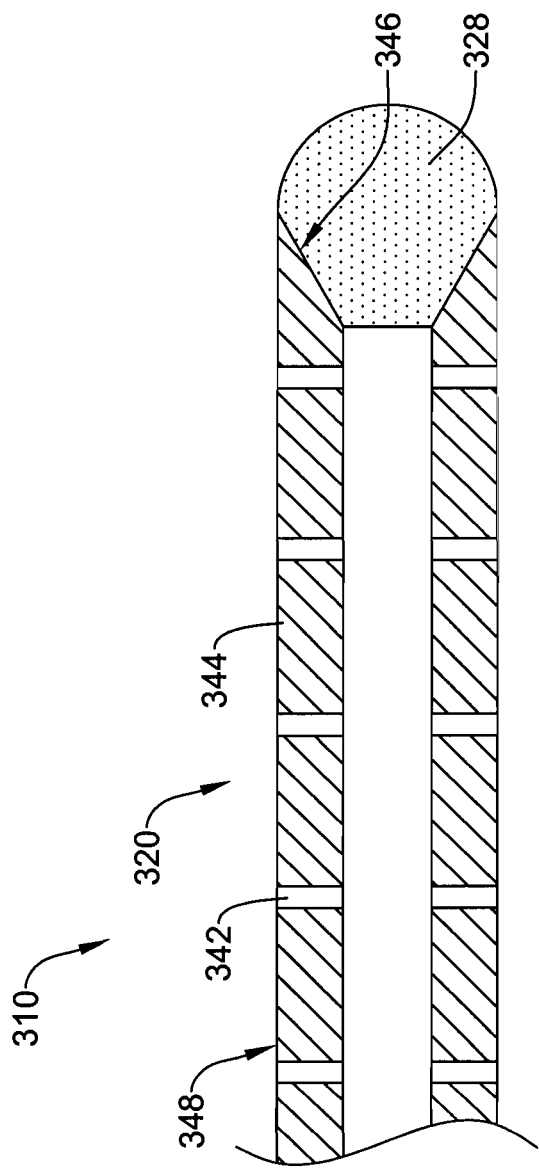
FIG. 17 is a cross-sectional side view of a portion of another example medical device.

FIG. 16 illustrates a portion of another example medical device 210 that includes tubular member 220 and tip member 228. Tubular member 220 may be similar to other tubular members disclosed herein and may includes slots 242 and tube wall 244. Tubular member 220 may also include region 248 having a substantially constant inner and outer diameter and tubular member 220 may include portions 246 where tube wall 244 thins. Similarly, FIG. 17 illustrates a portion of another example medical device 310 that includes tubular member 320 and tip member 328. Tubular member 320 may be similar to other tubular members disclosed herein and may includes slots 342 and tube wall 344. Tubular member 320 may also include region 348 having a substantially constant inner and outer diameter and tubular member 320 may include portions 346 where tube wall 344 thins.

The embodiments illustrated in FIGS. 16-17 demonstrate the use of tubular members 220/320 at the distal end or distal tip of devices 210/310. In the embodiment illustrated in FIG. 16, tube wall 244 thins along the exterior of tubular member 220. Conversely, in the embodiment illustrated in FIG. 17, tube wall 344 thins along the interior of tubular member 320. Both embodiments allow for a smooth transition from tubular member 220/320 to tip member 228/328. To further facilitate this transition, tip member 228/328 may overlap with thinned portion 246/346.

Figure 18:
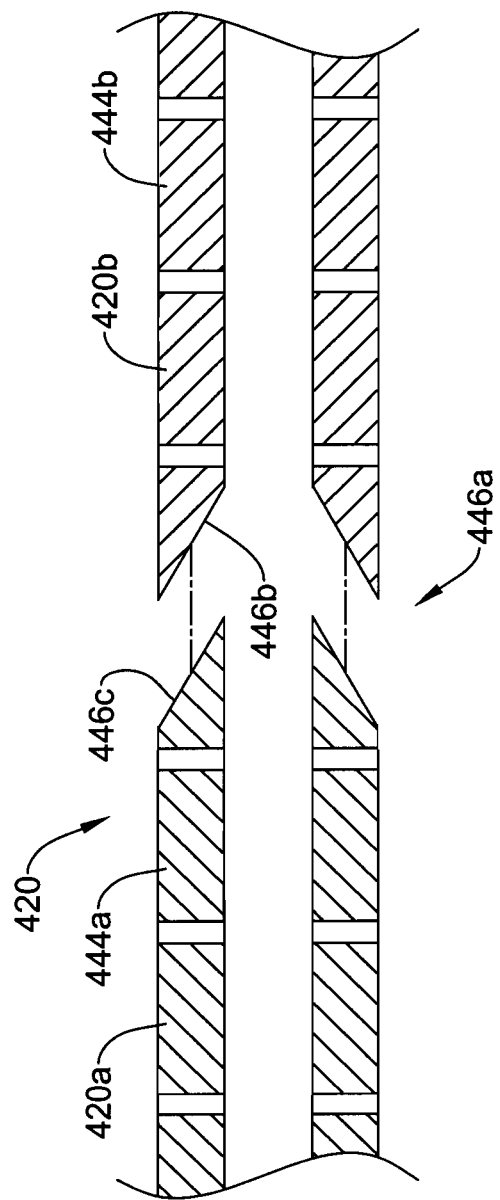
FIG. 18 is a cross-sectional side view of a portion of another example medical device.

FIG. 18 illustrates a portion of another example tubular member 420 that may be similar to other tubular member disclosed herein. Tubular member 420a may include section 420a and section 420b, which are shown in an exploded view. Section 420a may include portion 446a where tube wall 444a thins. Similarly, section 420*b* may include portion 446*b* where tube wall 444*b* thins. This embodiment illustrates that the thinning of the tube wall (e.g., tube wall 444*a*/444*b*) may be utilized to join together portions or sections of a tubular member. This may allow a number of tubular members or sections (e.g., sections 420*a*/420*b*) to be joined together. In at least some embodiments, sections 420*a*/420*b* may overlap or nest together. This may allow the flexibilities of sections 420*a*/420*b* (which may or may not be different) to be blended over a distance. It can be appreciated that one or more additional sections may be included in tubular member 420 and the additional section(s) may be attached to tubular member 420 in a similar manner.

The materials that can be used for the various components of guidewire 10 (and/or other guidewires disclosed herein) may include those commonly associated with medical devices. For simplicity purposes, the following discussion makes reference to tubular member 20 and other components of guidewire 10. However, this is not intended to limit the invention as the discussion may be applied to other similar tubular members and/or components of tubular members or devices disclosed herein.

Core wire 18, and/or tubular member 20, and/or connector 26, and/or tip member 28, and the like may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of MRI compatibility is imparted into guidewire 10. For example, to enhance compatibility with Magnetic Resonance Imaging (MRI) machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using any suitable connecting techniques and/or with connector 26. For example, the different portions of core wire 18 can be connected using welding (including laser welding), soldering, brazing, adhesive, or the like, or combinations thereof. These techniques can be utilized regardless of whether or not connector 26 is utilized. Connector 26 may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connector 26 including those connectors described in U.S. Pat. Nos. 6,918,882 and 7,071,197 and/or in U.S. Patent Pub. No. 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinyl-chloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18 and/or tubular member, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

The coating and/or sheath may be formed, for example, by coating, extrusion, co-extrusion, interrupted layer co-extrusion (ILC), or fusing several segments end-to-end. The same may be true of tip member 28. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
a metallic tubular member including a tube wall defining an inner diameter and having a wall thickness;
a core wire extending within and attached to the tubular member, the core wire having a distal portion with an outer surface;
wherein a gap is defined between the outer surface of the core wire and an inner surface of the tubular member;
wherein the tubular member has a plurality of slots formed therein;
wherein the tubular member includes a first portion having a first length and wherein the tube wall has a constant wall thickness across the first length;
wherein the tubular member includes a second portion, wherein the second portion is disposed at a distal end of the medical device, and wherein the second portion has a second length and wherein along an inner surface of the tubular member the tube wall thins in a curved manner so that the inner diameter increases distally across the second length;
wherein the length of the second portion is shorter than the length of the first portion; and wherein the distal portion of the core wire extends through the first portion of the tubular member and along the second length to a distal end of the second portion of the tubular member.

2. The medical device of claim 1, wherein across the second length, the tube wall thins in a linear manner.

3. The medical device of claim 1, wherein across the second length, the tube wall thins in a parabolic manner.

4. The medical device of claim 1, wherein across the second length, the tube wall thins in a stepped manner.

5. The medical device of claim 1, wherein across the second length, the tube wall thins that the outer diameter decreases across the second length.

6. The medical device of claim 1, further comprising a second metallic tubular member coupled to the second portion of the tubular member.

7. The medical device of claim 6, wherein the second metallic tubular member includes a tube wall and an outer diameter, wherein a third section of the second metallic tubular member has a third length, and wherein the tube wall of the second metallic tubular member thins so that the outer diameter of the second metallic tubular member decreases across the third length.

8. The medical device of claim 7, wherein the third section of the second tubular member is attached to the second section of the tubular member.

9. The medical device of claim 8, wherein the third second and the second section overlap.

10. The medical device of claim 1, further comprising a first core member and a second core member, and wherein the tubular member attaches the first core member to the second core member.

11. The medical device of claim 10, wherein the tubular member includes a third portion having a third length and wherein the tube wall thins so that the inner diameter increases across the third length.

12. The medical device of claim 11, wherein the second portion is disposed on a distal end of the tubular member and wherein the third portion is disposed on a proximal end of the tubular member.

13. The medical device of claim 1, wherein a distal end of the core wire is attached to a distal tip member.

14. The medical device of claim 1, wherein the tubular member has a constant outer diameter.

15. A method for manufacturing a medical device, the method comprising:
providing a metallic tubular member including a tube wall defining an inner diameter, the tubular member having a wall thickness, wherein the tubular member includes a first portion having a first length, wherein the tube wall has a constant wall thickness across the first length, wherein tubular member includes a second portion, wherein the second portion is disposed at a distal end of the tubular member, and wherein the second portion has a second length shorter than the first length;
providing a core wire, the core wire having a distal portion with an outer surface;
disposing the core wire within the tubular member, wherein a gap is defined between the outer surface of the core wire and an inner surface of the tubular member, wherein the core wire and the tubular member are attached to one another;
forming a plurality of slots in the tubular member;
thinning the second portion of the tubular member such that along an inner surface of the tubular member the tube wall thins in a curved manner and the inner diameter increases distally across the second length;
extending the core wire through the first portion of the tubular member and along the second length to a distal end of the second portion of the tubular member; and
wherein the second portion of the tubular member defines a distal end of the medical device.

16. A medical device, comprising:
a metallic tubular member including a tube wall defining an inner diameter and having a wall thickness;
a core wire extending within and attached to the tubular member, the core wire having a distal portion with an outer surface;
wherein a gap is defined between the outer surface of the core wire and an inner surface of the tubular member;
wherein the tubular member has a plurality of slots formed therein;
wherein the tubular member includes a first portion having a first length and wherein the tube wall has a constant wall thickness across the first length;
wherein the tubular member includes a second portion, wherein the second portion is disposed at a distal end of the medical device, and wherein the second portion has a second length and wherein along an inner surface of the tubular member the tube wall thins in a curved manner so that the inner diameter increases distally across the second length; and
wherein the length of the second portion is shorter than the length of the first portion.

17. The medical device of claim 16, wherein the tubular member has a constant outer diameter.

* * * * *

UNITED STATES PATENT AND TRADEMARK OFFICE
CERTIFICATE OF CORRECTION

| | | |
|---|---|---|
| PATENT NO. | : 8,535,243 B2 | Page 1 of 1 |
| APPLICATION NO. | : 12/207842 | |
| DATED | : September 17, 2013 | |
| INVENTOR(S) | : Brice L. Shireman | |

It is certified that error appears in the above-identified patent and that said Letters Patent is hereby corrected as shown below:

In the Specification

Column 1, Line 10: Delete "intracorporal" and insert therefor -- intracorporeal --.

Column 1, Line 15: Delete "intracorporal" and insert therefor -- intracorporeal --.

Signed and Sealed this
Fifteenth Day of April, 2014

Michelle K. Lee
*Deputy Director of the United States Patent and Trademark Office*